(12) United States Patent
El-Araby et al.

(10) Patent No.: US 10,888,566 B1
(45) Date of Patent: Jan. 12, 2021

(54) **CHEMOSENSITIZATION OF RESISTANT *PSEUDOMONAS AERUGINOSA* BY SYNTHETICALLY RELATED COMPOUNDS**

(71) Applicant: King Abdulaziz University, Jeddah (SA)

(72) Inventors: Moustafa E. El-Araby, Jeddah (SA); Abdelsattar M. Omar, Jeddah (SA); Mahmoud A. Elfaky, Jeddah (SA); Maan T. Khayat, Jeddah (SA); Ghufran A. Alhowswi, Jeddah (SA); Fatma M. Alhaity, Jeddah (SA); Muna M. Albeeshy, Jeddah (SA)

(73) Assignee: KING ABDULAZIZ UNIVERSITY, Jeddah (SA)

(*) Notice: Subject to any disclaimer, the term of this patent is extended or adjusted under 35 U.S.C. 154(b) by 0 days.

(21) Appl. No.: 17/065,025

(22) Filed: Oct. 7, 2020

Related U.S. Application Data

(62) Division of application No. 16/736,128, filed on Jan. 7, 2020, now Pat. No. 10,842,795.

(51) Int. Cl.
| | | |
|---|---|---|
| *A61K 31/5375* | (2006.01) | |
| *A61P 31/04* | (2006.01) | |
| *A61K 31/167* | (2006.01) | |
| *C07D 207/09* | (2006.01) | |
| *A61K 45/06* | (2006.01) | |
| *C07C 233/29* | (2006.01) | |
| *C07C 233/25* | (2006.01) | |
| *A61K 31/496* | (2006.01) | |
| *A61K 31/40* | (2006.01) | |
| *C07D 265/30* | (2006.01) | |

(52) U.S. Cl.
CPC ........ *A61K 31/5375* (2013.01); *A61K 31/167* (2013.01); *A61K 31/40* (2013.01); *A61K 31/496* (2013.01); *A61K 45/06* (2013.01); *A61P 31/04* (2018.01); *C07C 233/25* (2013.01); *C07C 233/29* (2013.01); *C07D 207/09* (2013.01); *C07D 265/30* (2013.01)

(58) Field of Classification Search
None
See application file for complete search history.

(56) References Cited

U.S. PATENT DOCUMENTS 10,710,957 B2 * 7/2020 Phanstiel, IV ........ C07C 211/17

* cited by examiner

*Primary Examiner* — Kamal A Saeed
(74) *Attorney, Agent, or Firm* — W&C IP

(57) ABSTRACT

Compounds for the chemosensitization of antibiotic resistant bacteria such as multidrug resistant (MDR) *Pseudomonas aeruginosa* (Pa) are provided. The compounds inhibit the MDR efflux proteins and re-sensitize the bacteria towards killing by antibiotics. Thus, the compounds are used in combination with antibiotics to treat or prevent infections caused by MDR bacteria.

10 Claims, 8 Drawing Sheets

CHEMOSENSITIZATION OF RESISTANT *PSEUDOMONAS AERUGINOSA* BY SYNTHETICALLY RELATED COMPOUNDS

BACKGROUND OF THE INVENTION

Field of the Invention

The invention generally relates to new compounds for the chemosensitization of antibiotic resistant bacteria. In particular, the new compounds inhibit the MDR efflux protein and re-sensitize the bacteria, e.g. *Pseudomonas aeruginosa* and related bacteria towards killing by antibiotics.

Description of Related Art

Resistant pathogenic bacteria have been weighing heavily on human and animal health (Tacconelli, Carrara et al. 2018). The decline in the effectiveness of antibiotics is dragging the humanity to pre-antibiotic era when communicable diseases caused mass life losses and lower life expectancy (Adedeji 2016). The World Health Organization (WHO) report titled "Ten threats to global health in 2019" placed antimicrobial resistance as the $5^{th}$ most challenging global health threat and it is a strong candidate to top the list (2019). In another report, the WHO recently published a list of 12 most dangerous pathogenic bacteria, in addition to resistant tuberculosis (Venter 2019). In this report, resistant *Pseudomonas aeruginosa* (Pa) appeared in the highest risk category "Priority: Critical" that urgently need new strategies to overcome their resistance to existing antibiotics (Venter 2019).

Pa is a major source of nosocomial infection especially in patients with burns, ventilator pneumonia and post-surgery wound infections (Wieland, Chhatwal et al. 2018). This dangerous pathogen has become highly resistant to most of available antibiotics and, therefore, it causes high rate of fatalities (Matos, Andriolo et al. 2018). Mechanisms of bacterial resistance include, but not limited to, loss of permeability of antibiotics due to a very active membrane efflux system. In multidrug resistant Pa (MDR-Pa), the efflux system is a transmembrane protein assembly that belong to the family Resistance Nodulation and cell Division (RND) efflux protein (FIG. 1). The RND system is tripartite assembly of an inner membrane protein called MexB that spans through the inner bacterial cell membrane and it is responsible for identifying substrates pumping them out. The outer membrane factor (OMF) named MexA is responsible of forcing the expelled antibiotic one way to outside. MexA/B are connected by a periplasmic compartment called OprM (Daury, Orange et al. 2016).

SUMMARY OF THE INVENTION

This disclosure provides compounds for the prevention and treatment of infections caused by bacteria which possess an efflux system for eliminating antibiotics that would otherwise be retained in the bacteria and kill or harm the bacteria. In particular, new compounds are described that inhibit Multidrug resistance pumps (MDR pumps) efflux proteins and re-sensitize MDR bacteria to antibiotics. Furthermore, in some aspects, the compounds showed good selectivity against bacterial efflux protein over human efflux protein, for example, the exemplary compound (N-((2Z,4E)-1-morpholino-1-oxo-5-phenylpenta-2,4-dien-2-yl)cinnamamide). In some exemplary aspects, the bacteria are *Pseudomonas aeruginosa* and the antibiotic is ciprofloxacin.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

It is an object of this invention to provide a compound of Formula I:

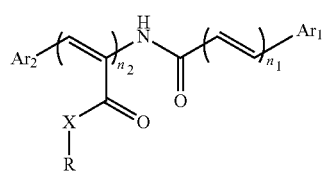

FORMULA I and salts (e.g. a pharmaceutically acceptable salt), hydrates and stereoisomers thereof, wherein Ar1 and Ar2 may be the same or different and are a substituted or unsubstituted aryl or heteroaryl;

X is i) N, O, S or C and R is substituted or unsubstituted, saturated or unsaturated, branched or unbranched C1-C10 alkyl; a 5-8 carbon unicyclic ring that is substituted or unsubstituted, saturated or unsaturated, cyclic alkyl or heterocyclic; or a 10-12 carbon polycyclic ring that is substituted or unsubstituted, saturated or unsaturated, cyclic alkyl or heterocyclic;

or ii) X and R are atoms of a 5-8 carbon unicyclic ring that is substituted or unsubstituted, saturated or unsaturated, cyclic alkyl or heterocyclic; or a 10-12 carbon polycyclic ring that is substituted or unsubstituted, saturated or unsaturated, and cyclic alkyl or heterocyclic;

and n1 and n2 are the same or different and =1 or 2.

In some aspects, Ar1 and Ar2 are phenyl; n1=1; n2=2; and X=N or O. In other aspects, X=N and R=substituted or unsubstituted, saturated or unsaturated, branched or unbranched C1-C10 alkyl; substituted phenyl; or N and R are atoms in a ring structure. In further aspects, X=O and R=substituted or unsubstituted, saturated or unsaturated, branched or unbranched C1-C10 alkyl. In still further aspects, the compound is

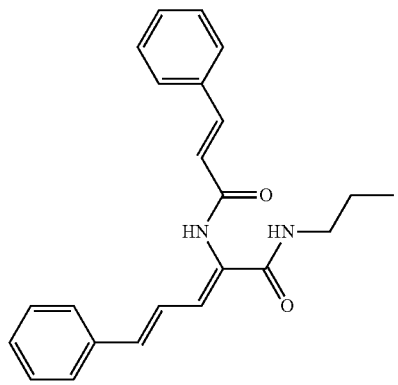

CAB-30

CAB-32
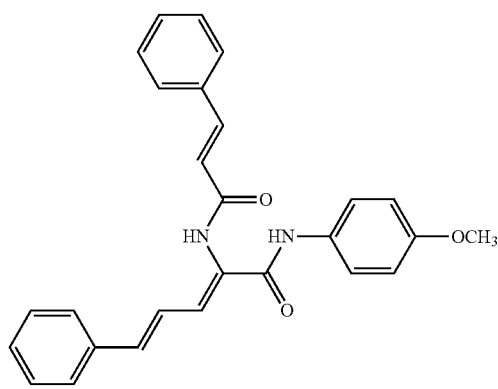
CAB-35
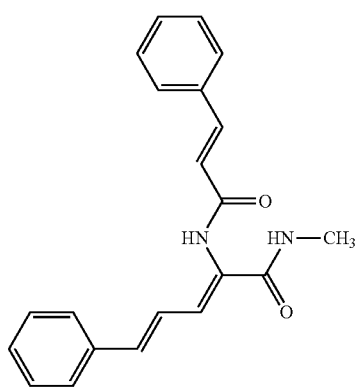
CAB-36
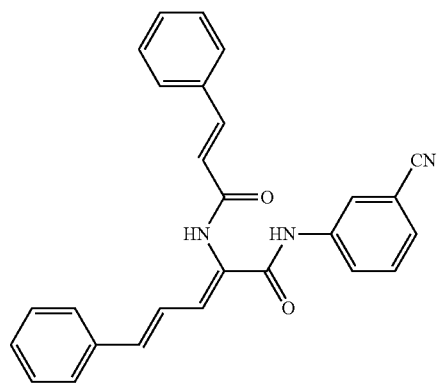
CAB-37
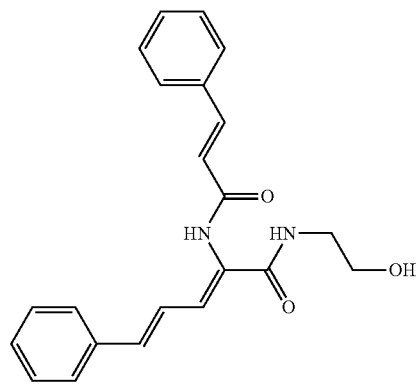
CAB-38
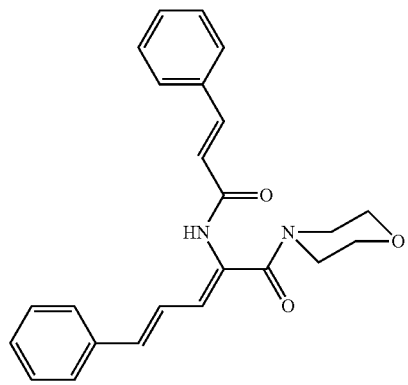
CAB-40
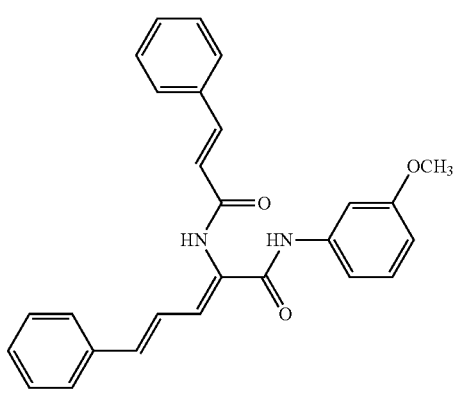
CAB-41
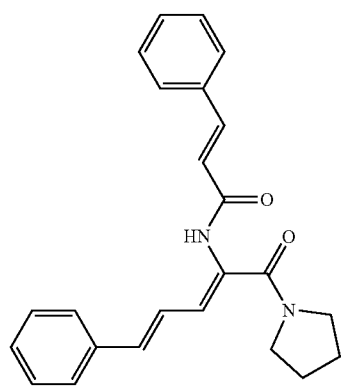
CAB-42
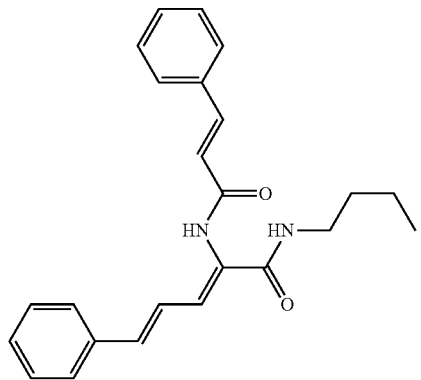

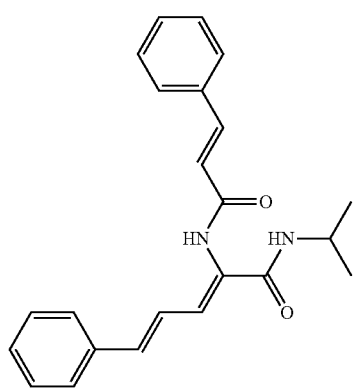

CAB-43 or

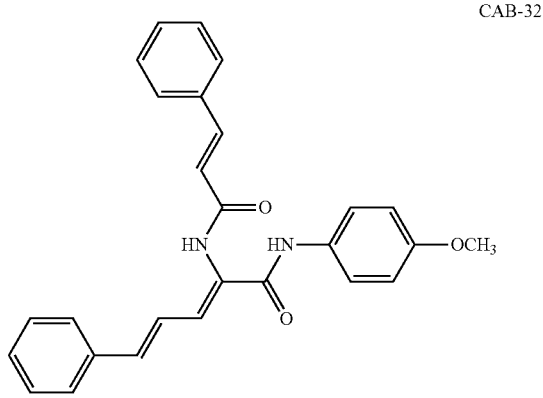

CAB-32

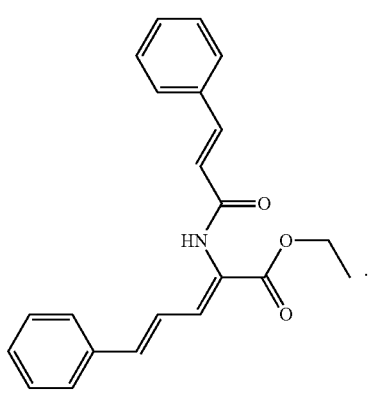

CAB-21

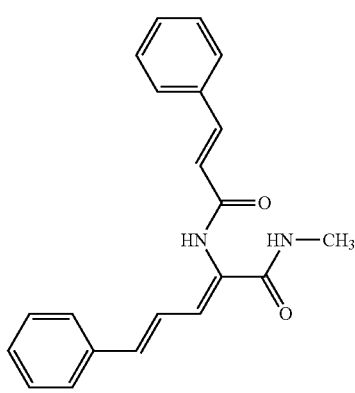

CAB-35

Also provided are methods of preventing or treating an infection caused by *Pseudomonas aeruginosa* (Pa) in a subject in need thereof, comprising administering to the subject a compound of Formula I and an antibiotic. In some aspects, the Pa is a multidrug resistant (MDR) Pa. In further aspects, Ar1 and Ar2 are phenyl; n1=1; n2=2; and X=N or O. In additional aspects, X=N and R=substituted or unsubstituted, saturated or unsaturated, branched or unbranched C1-C10 alkyl; substituted phenyl; or N and R are atoms in a ring structure. In additional aspects, X=O and R=substituted or unsubstituted, saturated or unsaturated, branched or unbranched C1-C10 alkyl. In some aspects, the compound is

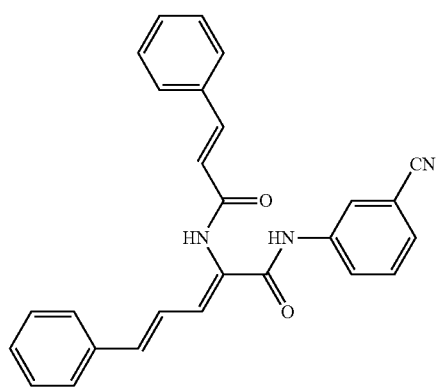

CAB-36

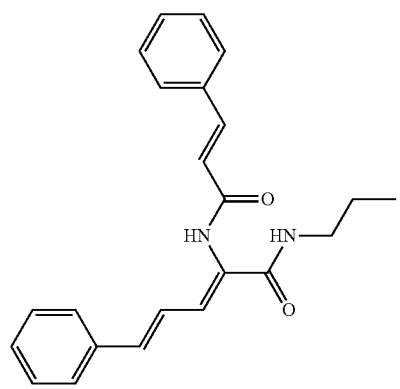

CAB-30

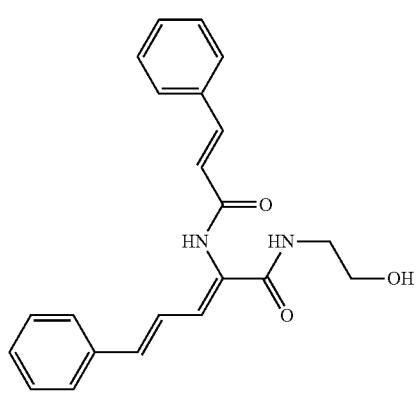

CAB-37

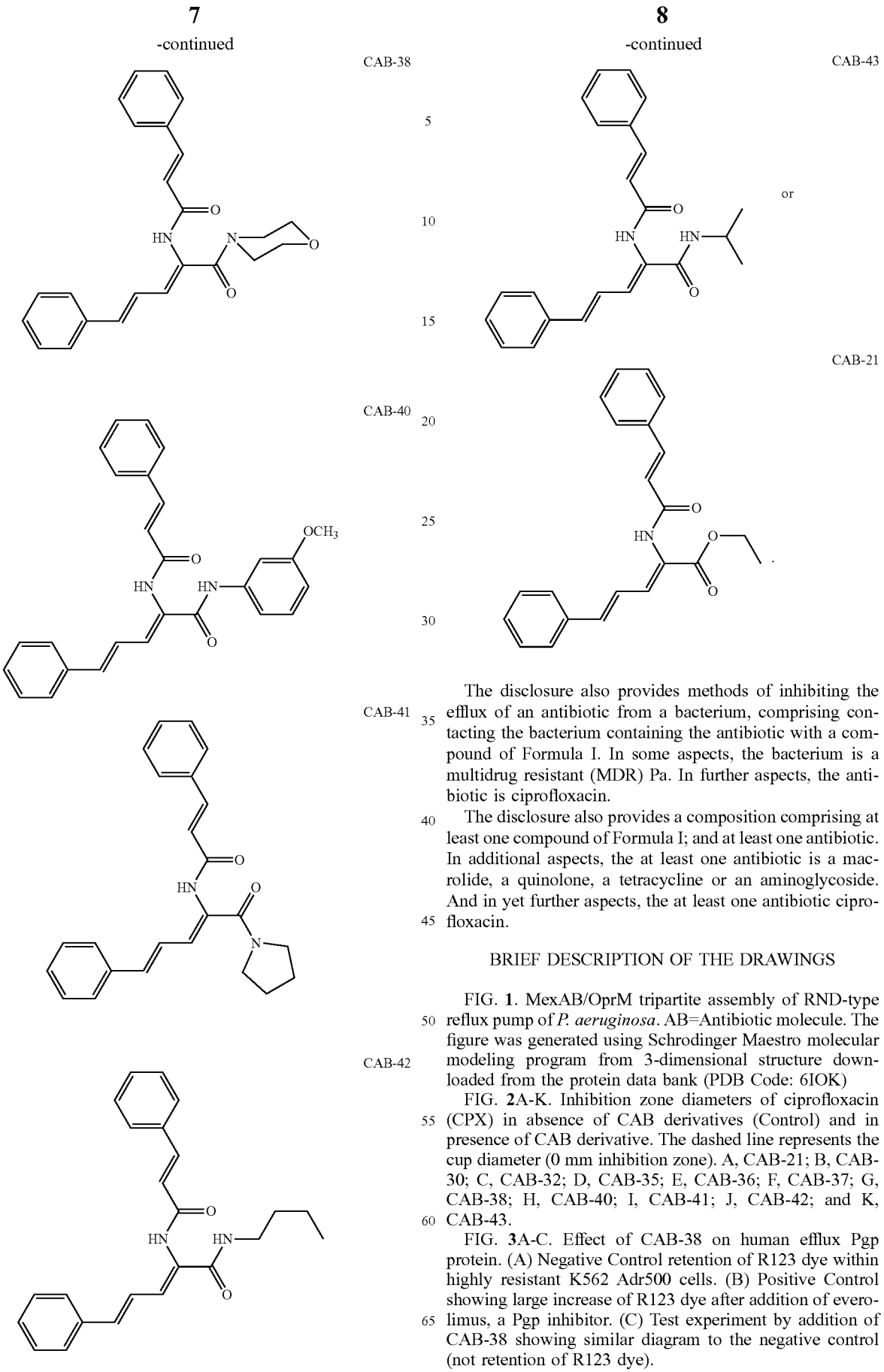

The disclosure also provides methods of inhibiting the efflux of an antibiotic from a bacterium, comprising contacting the bacterium containing the antibiotic with a compound of Formula I. In some aspects, the bacterium is a multidrug resistant (MDR) Pa. In further aspects, the antibiotic is ciprofloxacin.

The disclosure also provides a composition comprising at least one compound of Formula I; and at least one antibiotic. In additional aspects, the at least one antibiotic is a macrolide, a quinolone, a tetracycline or an aminoglycoside. And in yet further aspects, the at least one antibiotic ciprofloxacin.

DETAILED DESCRIPTION

Figure 1:
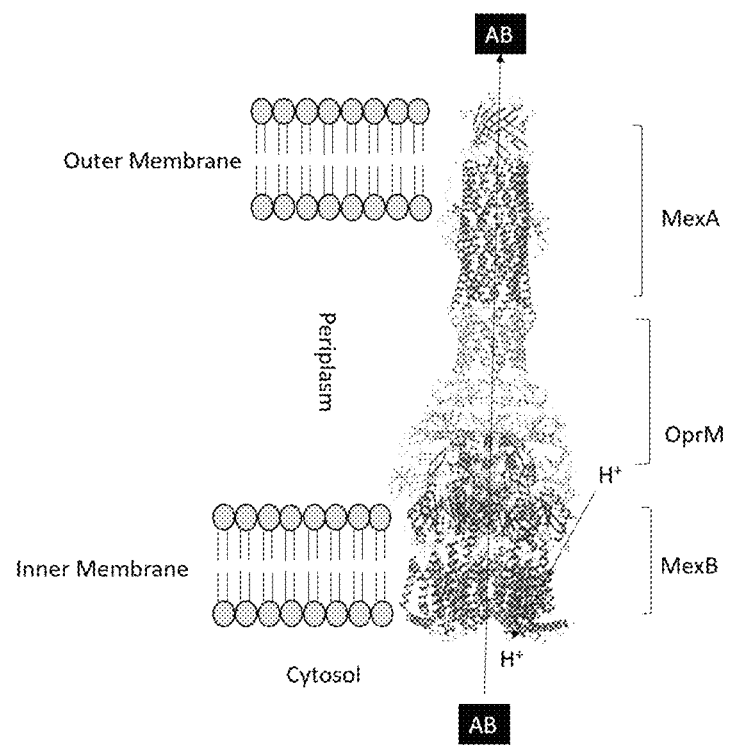
FIG. 1. MexAB/OprM tripartite assembly of RND-type reflux pump of *P. aeruginosa*. AB=Antibiotic molecule. The figure was generated using Schrodinger Maestro molecular modeling program from 3-dimensional structure downloaded from the protein data bank (PDB Code: 6IOK)
Figure 2A:
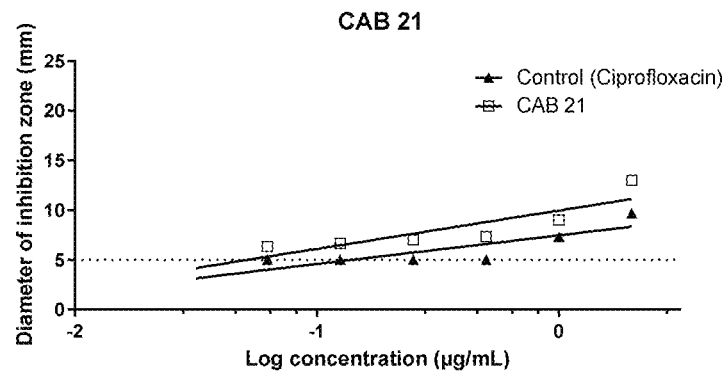
FIG. 2A-K. Inhibition zone diameters of ciprofloxacin (CPX) in absence of CAB derivatives (Control) and in presence of CAB derivative. The dashed line represents the cup diameter (0 mm inhibition zone). A, CAB-21; B, CAB-30; C, CAB-32; D, CAB-35; E, CAB-36; F, CAB-37; G, CAB-38; H, CAB-40; I, CAB-41; J, CAB-42; and K, CAB-43.
Figure 2B:
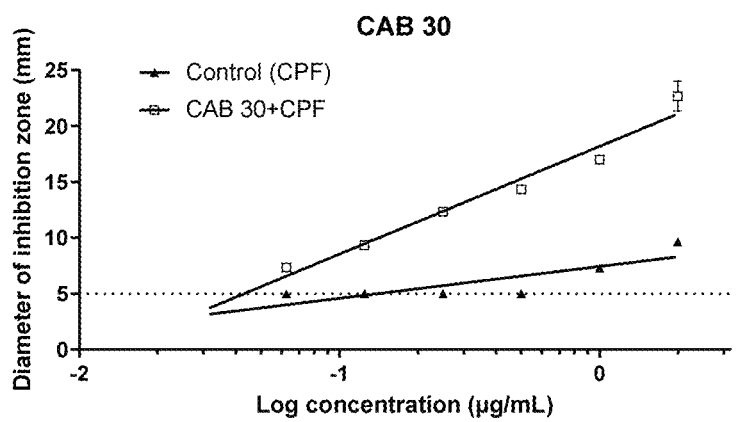
Figure 2C:
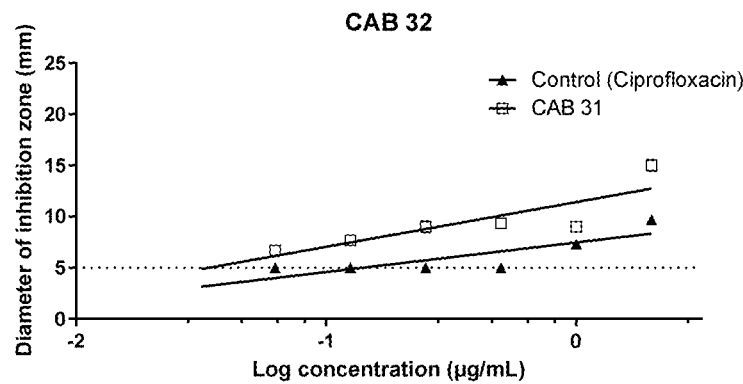
Figure 2D:
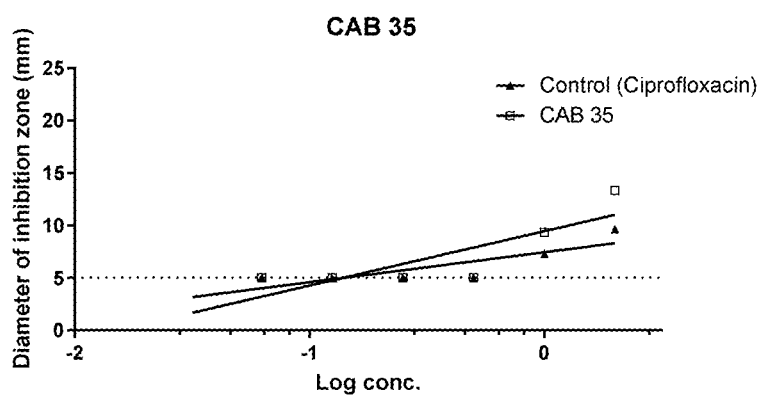
Figure 2E:
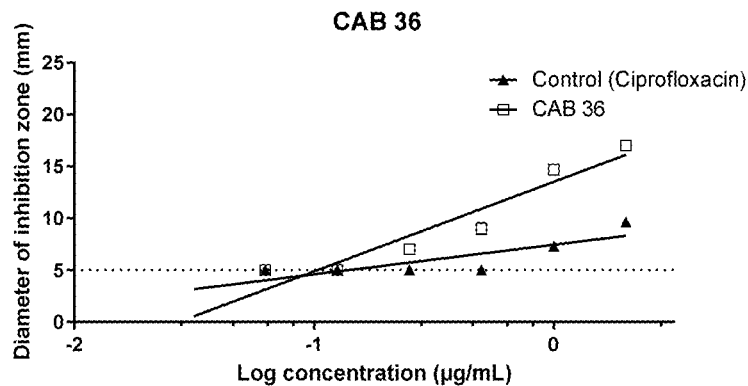
Figure 2F:
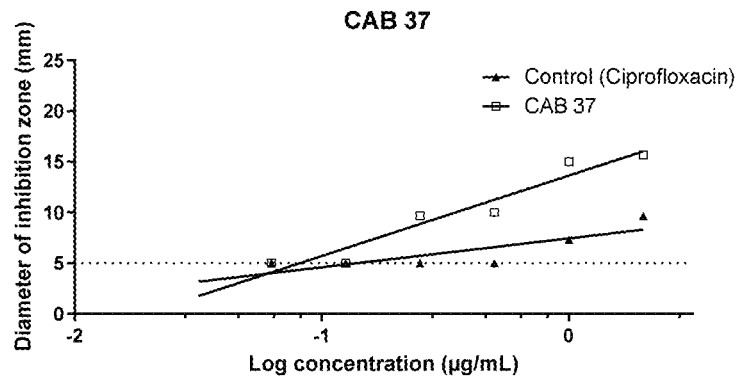
Figure 2G:
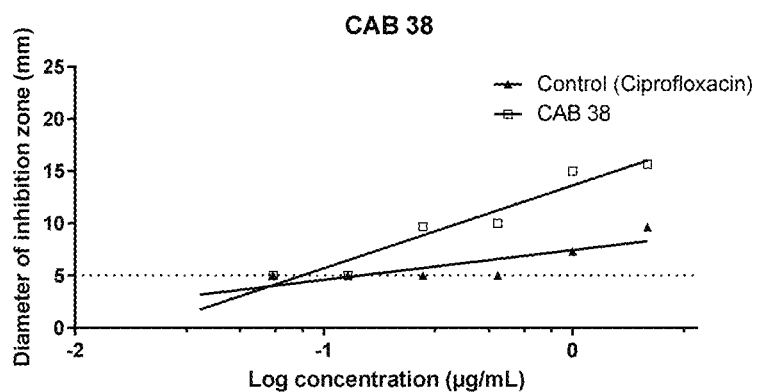
Figure 2H:
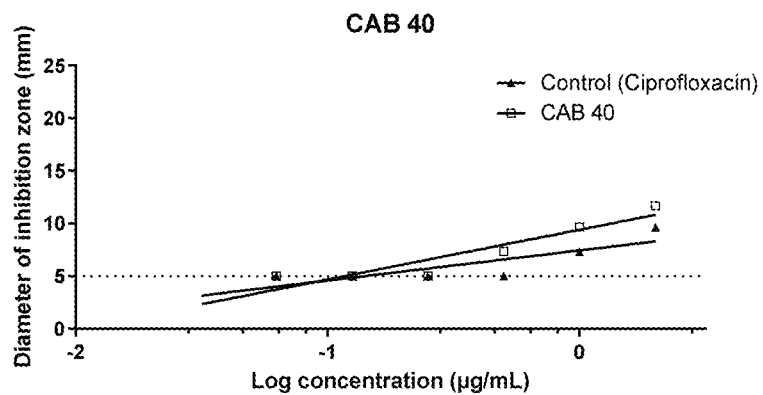
Figure 2I:
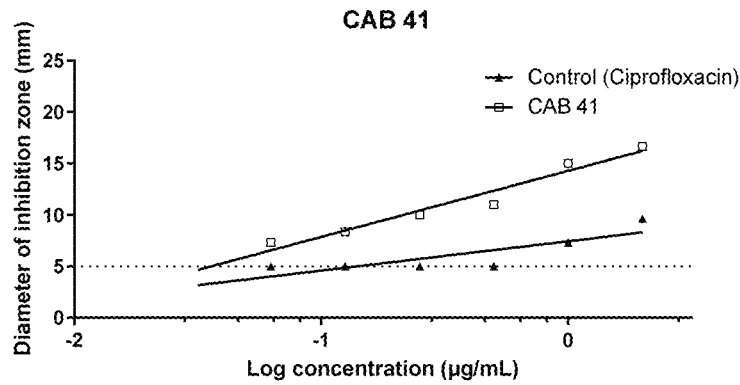
Figure 2J:
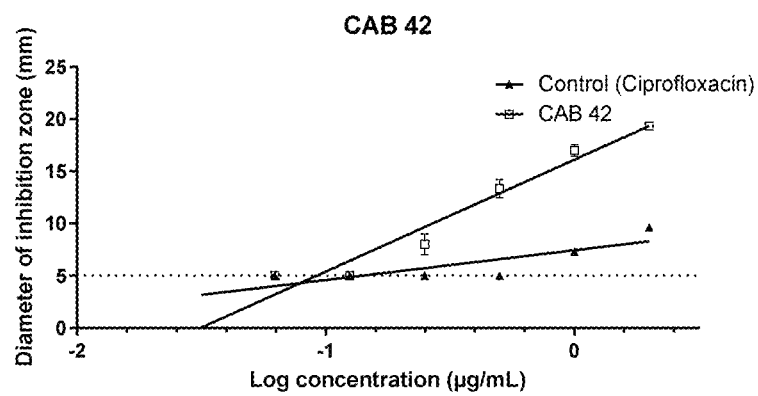
Figure 2K:
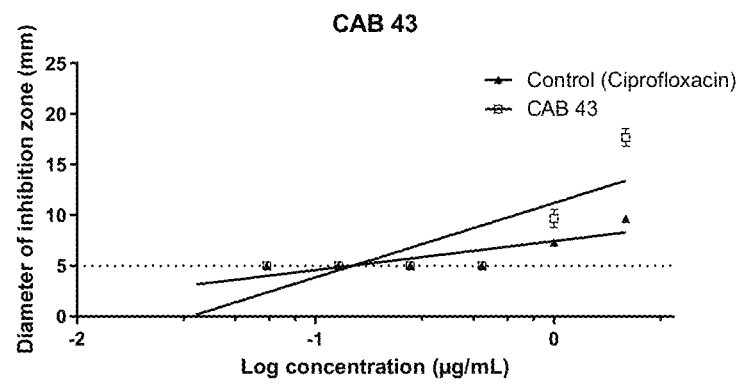

Provided herein are compounds for overcoming the antibiotic resistance of MDR bacteria which employ efflux pumps to avoid the action of antibiotics. In some aspects, the bacterium is an MDR Pa and the efflux pumps are selectively inhibited, e.g. without inhibiting, or inhibiting to a lesser extent, human pGp efflux proteins.

The compounds have generic Formula I:

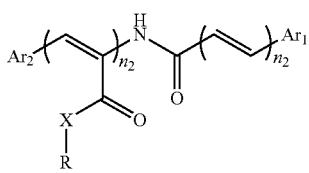

FORMULA I and salts (e.g. a pharmaceutically acceptable salt), hydrates and stereoisomers thereof, wherein Ar1 and Ar2 may be the same or different and are a substituted or unsubstituted aryl or heteroaryl;

X is i) N, O, S or C; and R is substituted or unsubstituted, saturated or unsaturated, branched or unbranched C1-C10 alkyl; a 5-8 carbon unicyclic ring that is substituted or unsubstituted, saturated or unsaturated, cyclic alkyl or heterocyclic; or a 10-12 carbon polycyclic ring that is substituted or unsubstituted, saturated or unsaturated, cyclic alkyl or heterocyclic;

or ii) X and R are atoms of a 5-8 carbon unicyclic ring that is substituted or unsubstituted, saturated or unsaturated, cyclic alkyl or heterocyclic; or a 10-12 carbon polycyclic ring that is substituted or unsubstituted, saturated or unsaturated, and cyclic alkyl or heterocyclic;

and n1 and n2 are the same or different and =1 or 2.

Ar1 and Ar2 are, for example, phenyl, naphthyl, pyridyl, indolyl, thienyl, furyl, pyrimidinyl, quinolinyl (substituted with alkyl (C1 to C5), CN, F, Cl, Br, CF$_3$, OR1 where R1 is methyl, ethyl, n-propyl or isopropyl, or NR2R3, where R2 and R3 are the same or different and are methyl, ethyl, n-propyl or isopropyl.

In some aspects, substituted or unsubstituted, branched or unbranched C1-C10 alkyl is methyl, ethyl, propyl (n-propyl, iso-propyl), butyl (n-butyl, sec-butyl, iso-butyl, tert-butyl), pentyl (n-pentyl, isopentyl, neopentyl).

In some aspect, the C1-C10 alkyl is substituted with 0, N or S or a cyclic structure such as phenyl, pyridyl, indolyl, thienyl, furyl, pyrimidinyl, quinolinyl (substituted with alkyl (C1 to C5), CN, F, Cl, Br, CF$_3$, OR1 where R1 is methyl, ethyl, n-propyl or isopropyl, or NR2R3, where R2 and R3 are the same or different and are methyl, ethyl, n-propyl or isopropyl. If the cyclic structure is substituted phenyl, the substitution(s) may be ortho, meta or para on the ring The term unicyclic and polycyclic refer to rings with, for example, from about 5-8 or about 10-12 atoms, respectively. The rings may be carbocyclic (containing only carbon atoms) or heterocyclic, containing at least one hetero (non-carbon) atoms. For example, heterocyclic refers to a ring containing at least one heteroatom (e.g. 1-3 heteroatoms) independently selected from the group consisting of O, N, and S. If unsaturated, the ring can comprise one or more double bonds, e.g. 1-3 double bonds. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle can be a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, azabicyclo[2.2.1]heptyl (including 2-azabicyclo[2.2.1]hept-2-yl), 2,3-dihydro-1H-indolyl, isoindolinyl, octahydrocyclopentaclpyrrolyl, octahydropyrrolopyridinyl, and tetrahydroisoquinolinyl. The monocyclic and bicyclic heterocycles are connected to the parent molecular moiety through any carbon atom contained within the rings.

In some aspects, N and R form part of a ring system. Examples of suitable ring systems include but are not limited to: saturated and unsaturated C5-C7 rings which may be cyclic alkyl or heteroalkyl. If heteroalkyl, the heteroatoms may be N, O or S, and one or more heteroatoms may be present. In some aspects, the heteroalkyl ring is a 5-membered ring with N as the heteroatom; in other aspects, the heteroalkyl ring is a 6-membered ring with N and O as heteroatoms.

In some aspects, Ar1 and Ar2 are phenyl; n1=1; n2=2; and X=N or O.

In some aspects, Ar1 and Ar2 are phenyl; n1=1; n2=2; X=N and R=CH$_3$ (CAB-35); CH$_2$CH$_2$CH$_3$ (CAB-30); CH$_2$CH$_2$CH$_2$CH$_3$ (CAB-42); CH$_2$CH$_2$OH (CAB-37); isopropyl (CAB-43); substituted phenyl such as phenyl substituted with CN at the meta position (CAB-36), or with OCH3 at the meta position (CAB-40) or the para position (CAB-32); or N and R are atoms in a ring structure such as pyrrolidine (CAB-41) or oxazine (CAB-38).

In some aspects, Ar1 and Ar2 are phenyl; n1=1; n2=2; X=O and R=CH$_2$CH$_3$ (CAB-21).

In some aspects, R is not ethyl.

In some exemplary aspects, the new compounds are:
CAB-30
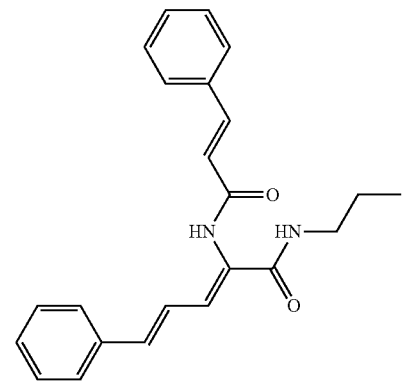
CAB-32
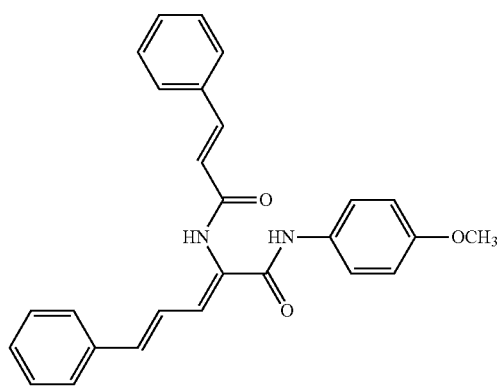
CAB-35
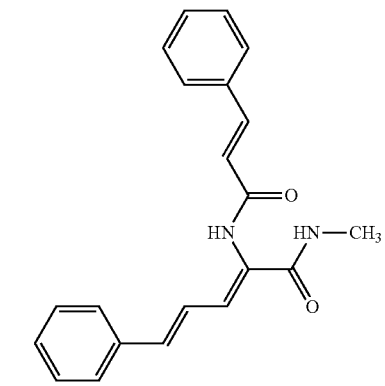
CAB-36
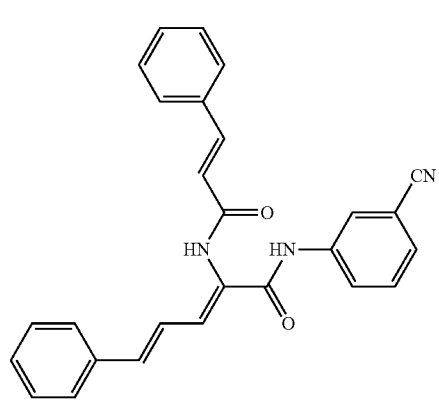
CAB-37
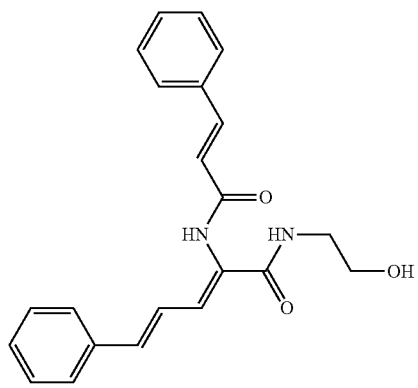
CAB-38
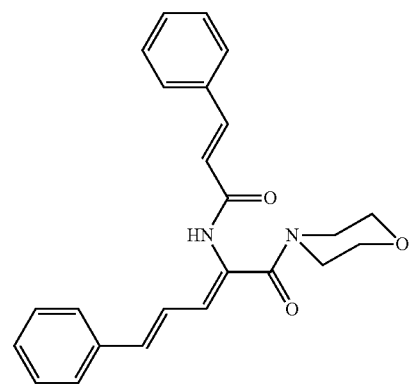
CAB-40
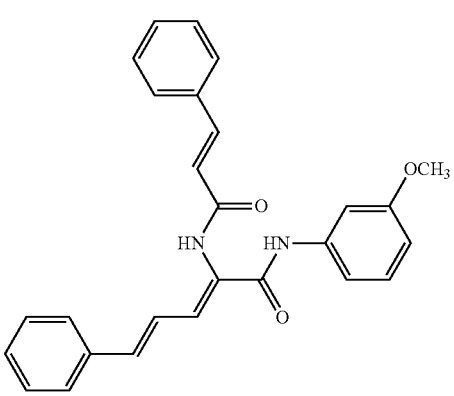
CAB-41
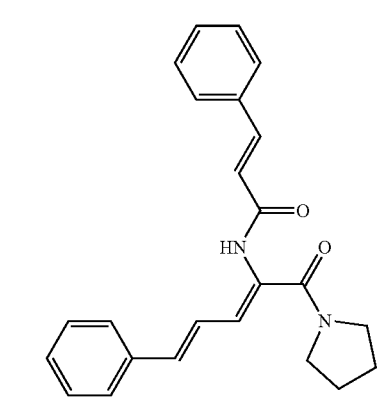

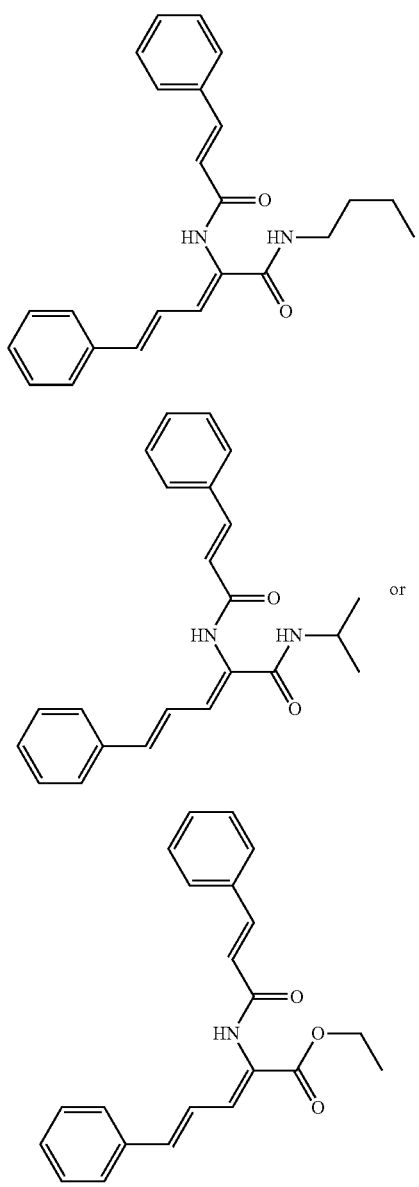

CAB-42

CAB-43

CAB-21

Compositions and Administration

The disclosure also provides methods of preventing or treating infections in subjects with a bacterial infection, e.g. an infection with an MDR bacterium. The methods comprise administering to the subject a therapeutically effective amount of at least one compound disclosed herein, in combination with an antibiotic. The compounds described herein are generally delivered (administered) as a pharmaceutical composition. Such pharmaceutical compositions generally comprise at least one of the disclosed compounds, i.e. one or more than one (a plurality) of different compounds (e.g. 2 or more such as 2, 3, 4, 5, 6, 7, 8, 9, 10 or more) may be included in a single formulation. Accordingly, the present invention encompasses such formulations/compositions. The compositions generally include one or more substantially purified compounds as described herein, and a pharmacologically suitable (physiologically compatible) carrier. In some aspects, such compositions are prepared as liquid solutions or suspensions, or as solid forms such as tablets, pills, powders and the like. Solid forms suitable for solution in, or suspension in, liquids prior to administration are also contemplated (e.g. lyophilized forms of the compounds), as are emulsified preparations. In some aspects, the liquid formulations are aqueous or oil-based suspensions or solutions. In some aspects, the active ingredients are mixed with excipients which are pharmaceutically acceptable and compatible with the active ingredients, e.g. pharmaceutically acceptable salts. Suitable excipients include, for example, water, saline, dextrose, glycerol, ethanol and the like, or combinations thereof. In addition, the composition may contain minor amounts of auxiliary substances such as wetting or emulsifying agents, pH buffering agents, preservatives, and the like. If it is desired to administer an oral form of the composition, various thickeners, flavorings, diluents, emulsifiers, dispersing aids or binders and the like are added. The composition of the present invention may contain any such additional ingredients so as to provide the composition in a form suitable for administration. The final amount of compound in the formulations varies but is generally from about 1-99%. Still other suitable formulations for use in the present invention are found, for example in Remington's Pharmaceutical Sciences, 22nd ed. (2012; eds. Allen, Adejarem Desselle and Felton).

Some examples of materials which can serve as pharmaceutically acceptable carriers include, but are not limited to, ion exchangers, alumina, aluminum stearate, lecithin, serum proteins (such as human serum albumin), buffer substances (such as twin 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

"Pharmaceutically acceptable salts" refers to the relatively non-toxic, inorganic and organic acid addition salts, and base addition salts, of compounds of the present invention. These: salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-.beta.-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. See, for example S. M. Berge, et al., "Pharmaceutical Salts," J. Pharm. Sci., 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

The compositions may be administered in vivo by any suitable route including but not limited to: by injection (e.g. intravenous, intraperitoneal, intramuscular, subcutaneous, and the like); by absorption through epithelial or mucocutaneous linings (e.g., nasal such as by inhalation, oral, rectal, gastrointestinal mucosa, and the like); topically (especially for a skin infection); orally (e.g. as a pill, capsule, liquid, etc.), etc. In preferred embodiments, the mode of administration is oral or by injection.

In addition, the compositions may be administered in conjunction with other treatment modalities such as substances that boost the immune system, various chemotherapeutic agents, various antibiotic agents, and the like.

In particular, the compounds described herein are administered with at least one antibiotic, especially with an antibiotic to which the Pa would otherwise be resistant. Examples of antibiotics that may be administered with the compounds include but are not limited to:

macrolides such as azithromycin, clarithromycin, erythromycin, spiramycin, telithromycin, etc;

quinolones, especially fluoroquinolones such as ciprofloxacin, lomefloxacin, norfloxacin, ofloxacin, moxifloxacin, gatifloxacin, nalidixic acid, delafloxacin, gemifloxacin, cinoxacin, trovafloxacin, sparfloxacin, levofloxacin, etc;

tetracyclines such as doxycycline, demeclocycline, minocycline, oxytetracycline, tetracycline, omadacycline, sarecycline, eravacycline, etc.;

aminoglycosides such as gentamicin, tobramycin, amikacin, netilmicin, neomycin, isepamicin, arbekacin, kanamycin, streptomycin, neo-fradin, etc.

Any antibiotic that acts within the bacterial cell may be used in combination with the compounds described herein.

In some aspects, the antibiotic is ciprofloxacin.

Other possible antibiotics and methods of administration are described in US patent application 20190256452, the complete contents of which are hereby incorporated by referenced in entirety.

The specific therapeutically effective dose level for any particular patient will depend upon a variety of factors including the infection being treated and the severity of the infection; activity of the specific compound employed; the specific composition employed, the age, body weight, general health, sex and diet of the patient; the time of administration, route of administration, and rate of excretion of the specific compound employed; the duration of the treatment; drugs used in combination or coincidential with the specific compound employed; and like factors well known in the medical arts. For example, it is well known within the skill of the art to start doses of the compound at levels lower than those required to achieve the desired therapeutic effect and to gradually increase the dosage until the desired effect is achieved, or vice versa (start with a high dose and decrease as the infection subsides). The dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Typical dosages of antibiotics are known in the art.

The subject is generally a mammal, usually a human, and may be an adult or a child, e.g. especially an immunocompromised human. However, veterinary usage is also encompassed, e.g. in animals that are used as food sources or in pets, e.g. cats and dogs.

Infections that are Treated

Subjects that are treated with the compounds described herein are any who have an infection, or who are likely or will possibly have an infection, caused by a bacteria comprising an efflux pump system. Examples of such bacteria include but are not limited to: multidrug-resistant *Pseudomonas aeruginosa*, Methicillin/oxacillin-resistant *Staphylococcus aureus*, Vancomycin-resistant Enterococci, multidrug-resistant *Streptococcus pneumoniae*, multi-drug resistant *Mycobacterium tuberculosis*, Extended-spectrum beta-lactam resistant *Escherichia coli* (which are resistant to cephalosporins and monobactams), carbapenem-resistant Enterobacteriaceae, ampicillin resistant *Haemophilus influenza*, clarithromycin resistant *Helicobacter pylori*, fluoroquinolone resistant *Campylobacter* spp., fluoroquinolone resistant *Salmonella* spp., fluoroquinolone resistant *Shigella* spp., multidrug-resistant *Acinetobacter baumannii*, multidrug-resistant *Bacillus subtilis* and multidrug-resistant *Neisseria* gonorrhea.

In some aspects, infections are caused by bacteria that are over expressing efflux-pump protein, where the efflux pump protein belongs to one of the following families: resistance nodulation cell division (RND), Small multidrug resistance (SMR), major facilitator superfamily (MFS), multidrug and toxic compound extrusion (MATE) and ATP-binding cassette (ABC).

In some aspects, the efflux pump is of the RND family which includes, but is not limited to, MexAB-OprM, MexCDOprJ, MexEF-OprN, MexXY-OprM, MexPQ-OpmE, MexMN-OprM, and MexVW-OprM.

In some aspects, the bacteria is Pa. Pa is an opportunistic pathogen and takes advantage of an individual's weakened immune system to create an infection and produce tissue-damaging toxins. Pa is the most common pathogen isolated from patients who have been hospitalized for extended periods of time (e.g. longer than 1 week) and is a frequent cause of nosocomial infections, causing between 10% and 20% of infections in most hospitals. Epidemics have been traced to many items in the hospital environment.

Pa infection is especially prevalent among patients having and/or undergoing treatment for burn wounds, cystic fibrosis, and intravenous-drug addiction, and cancer (e.g. acute leukemia and AIDS) and organ transplant patients. In some aspects, the subjects are immunosuppressed, e.g. having neutropenia (a low level of neutrophils.

Pa causes urinary tract infections (UTIs), respiratory system infections such as pneumonia, dermatitis, soft tissue infections, bacteremia, bone and joint infections, gastrointestinal infections, a variety of systemic infections (e.g. septicemia), malignant external otitis, endophthalmitis, endocarditis, meningitis, etc. Any patient or subject who has one or more of these conditions or infection, or who is at risk of developing or contracting one of these infections, can be treated or prophylactically treated using one or more compounds as described herein.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLE

Methods:
Synthesis of Compounds

The intermediate 1 was synthesized according to reported procedure (El-Araby, Omar et al. 2017) and made available for the preparation of the final compounds following appropriate procedures (Schemes 1-3). The azlactone intermediate 1 was reacted with aliphatic amines in ethanol (Scheme 2) to obtain CAB-30 (El-Araby, Omar et al. 2017), CAB-37, CAB-38, CAB-41, CAB-42 and CAB-43.

Scheme 1. Synthesis of CAB compounds containing N-alkyl groups

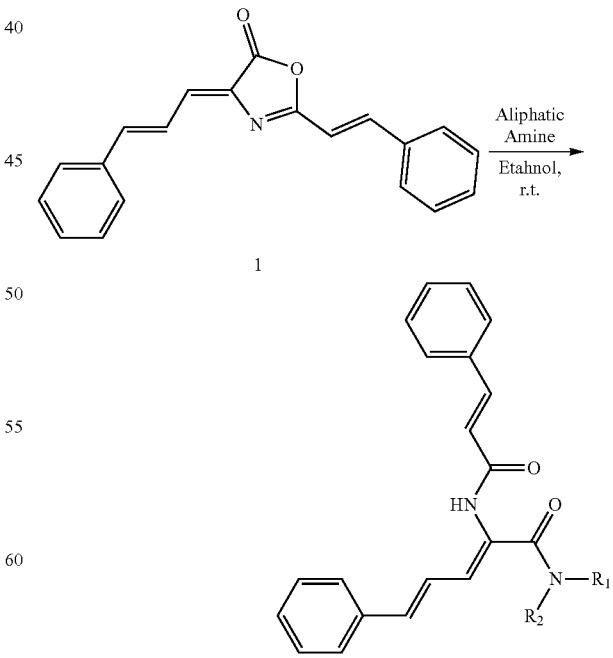

In a slightly different reaction, aromatic amines were reacted with 1 in N,N-dimethylformamide (DMF) as solvent at 100° C. to furnish CAB-32, CAB-36 and CAB-40 (Scheme-2).

Scheme 2. Synthesis of compounds containing aromatic amide

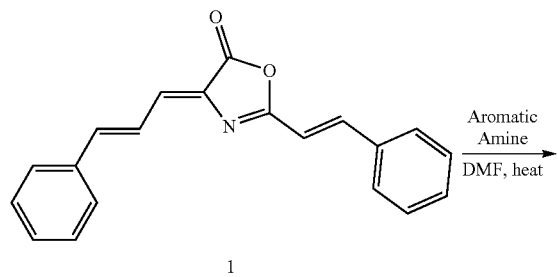

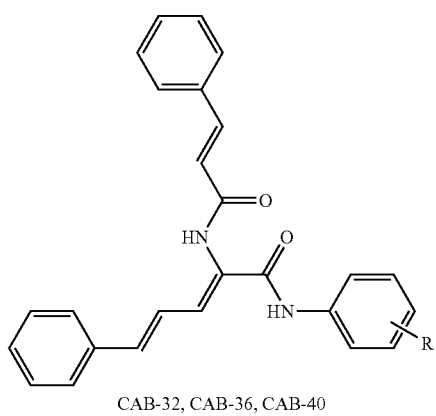

CAB-32, CAB-36, CAB-40

The alcohol derivative CAB-21 was prepared by ethanolysis of 1 in presence of catalytic amount of 4-(N,N-dimethyl) pyridine (DMAP).

Scheme 3. Synthesis of ester derivative CAB-21.

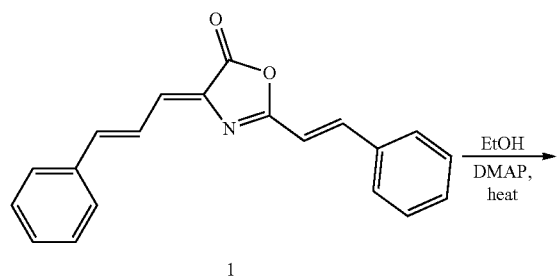

-continued

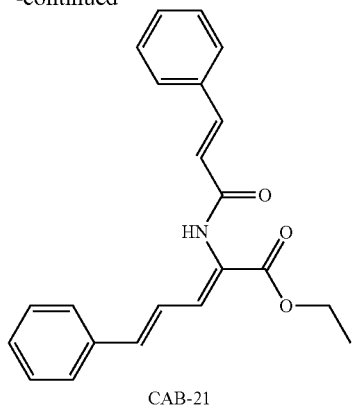

CAB-21

Experimental

All solvents and reagents were purchased from Merck KGaA, Darmstadt, Germany and used without further processing. An Agilent 6320 liquid chromatography-ion trap mass spectrometer (LC-IT-MS) was used for the characterization targeted compounds.

The MS system was connected to an HPLC-Agilent 1200 system equipped with an autosampler, a quaternary pump, and a column compartment (Palo Alto, Calif., USA). The system was equipped with ChemStation software (Rev. B.01.03 SR2(204)). The IT-MS was controlled using 6300 series trap control version 6.2 Build No. 62.24 (Bruker Daltonik GmbH), and the general MS adjustments were: capillary voltage, 4200 V; nebulizer, 37 psi; drying gas, 12 L/min; desolvation temperature, 330° C.; ion charge control (ICC) smart target, 200,000; and max accumulation time, 200 millisecond (ms). The MS scan range was 50-600 m/z. Auto-MSn positive mode was applied. Mobile system: isocratic elution with a mobile system composed of 64% acetonitrile: 20% methanol: 16% water containing 0.1% formic acid, at flow rate of 0.6 mL/min, injection volume, 2 µL.

Melting points were uncorrected and measured using the capillary melting point instrument BI 9100 (Barnstead Electrothermal, UK).

$^1$H NMR spectra were determined on an AVANCE-III 400 MHz and AVANCE-III HD 850 MHz spectrometers (Bruker, Germany), and chemical shifts are expressed as ppm against TMS as an internal reference (Faculty of Science, King Abdulaziz University, Jeddah, Saudi Arabia).

CAB-30 was reported by our research group (El-Araby, Omar et al. 2017).

General Procedure for Synthesis of N-Alkyl CAB Compounds Presented in Scheme 1 (CAB-35, CAB-37, CAB-38, CAB-41, CAB-42, CAB-43)

The azlactone 1 (0.01 mol) was placed in 20 mL ethanol and the appropriate aliphatic amine (0.02 mol) and the mixture was left to stir at r.t. for 2 h. After completion of the reaction as monitored by TLC, the precipitated solid compound was collected by filtration, washed with ethanol and crystallized from a mixture of dichloromethane and methanol.

(2Z,4E)-2-cinnamamido-N-methyl-5-phenylpenta-2,4-dienamide (CAB-35)

$^1$H NMR (850 MHz, DMSO-d$_6$) δ 9.71 (s, 1H), 7.96 (d, J=4.67 Hz, 1H), 7.64 (d, J=7.27 Hz, 2H), 7.50-7.54 (m, 3H), 7.45-7.49 (m, 2H), 7.41-7.45 (m, 1H), 7.37 (t, J=7.53 Hz,

2H), 7.27-7.31 (m, 1H), 7.00 (dd, J=11.42, 15.57 Hz, 1H), 6.85-6.94 (m, 2H), 6.77 (d, J=11.42 Hz, 1H), 2.67 (d, J=4.15 Hz, 2H).

(2Z,4E)-2-cinnamamido-N-(3-cyanophenyl)-5-phenylpenta-2,4-dienamide (CAB-36)

$^1$H NMR (850 MHz, DMSO-d$_6$) δ 10.02 (s, 1H), 8.18 (s, 1H), 7.99 (d, J=7.79 Hz, 1H), 7.65 (d, J=7.27 Hz, 1H), 7.51-7.60 (m, 4H), 7.47 (s, 2H), 7.37-7.45 (m, 5H), 7.31-7.37 (m, 2H), 7.20 (dd, J=11.42, 15.57 Hz, 1H), 7.00 (d, J=15.57 Hz, 1H), 6.91 (d, J=16.09 Hz, 1H).

(2Z,4E)-2-cinnamamido-N-(2-hydroxyethyl)-5-phenylpenta-2,4-dienamide (CAB-37)

$^1$H NMR (850 MHz, DMSO-d$_6$) δ 9.71 (s, 1H), 7.96 (br. s., 1H), 7.64 (d, J=7.27 Hz, 2H), 7.51-7.55 (m, 2H), 7.44-7.50 (m, 2H), 7.43 (d, J=7.27 Hz, 1H), 7.37 (t, J=7.78 Hz, 2H), 7.28-7.31 (m, 1H), 6.99-7.04 (m, 1H), 6.86-6.93 (m, 2H), 6.78 (s, 1H), 4.63 (t, J=5.45 Hz, 1H), 3.43-3.47 (m, 2H), 3.22 (q, J=6.23 Hz, 2H).

N-((2Z,4E)-1-morpholino-1-oxo-5-phenylpenta-2,4-dien-2-yl)cinnamamide (CAB-38)

$^1$H NMR (850 MHz, DMSO-d$_6$) δ 10.15 (s, 1H), 7.65 (d, J=7.27 Hz, 2H), 7.58 (d, J=15.57 Hz, 1H), 7.54 (d, J=7.27 Hz, 2H), 7.46 (d, J=7.27 Hz, 2H), 7.43 (s, 1H), 7.38 (t, J=7.79 Hz, 2H), 7.25-7.31 (m, 2H), 6.88 (d, J=15.57 Hz, 1H), 6.77 (d, J=15.57 Hz, 1H), 5.93 (d, J=11.42 Hz, 1H), 3.64 (br. s., 4H), 3.51 (br. s., 4H).

N-((2Z,4E)-1-oxo-5-phenyl-1-(pyrrolidin-1-yl)penta-2,4-dien-2-yl)cinnamamide (CAB-41)

$^1$H NMR (850 MHz, DMSO-d$_6$) δ 9.67 (s, 1H), 8.00 (t, J=5.45 Hz, 1H), 7.64 (d, J=7.27 Hz, 2H), 7.51-7.54 (m, 3H), 7.44-7.48 (m, 2H), 7.39-7.42 (m, 1H), 7.35-7.39 (m, 2H), 7.27-7.31 (m, 1H), 7.02 (dd, J=11.16, 15.83 Hz, 1H), 6.89-6.92 (m, 1H), 6.72 (d, J=11.42 Hz, 1H), 3.20-3.25 (m, 1H), 3.11-3.15 (m, 2H), 0.94 (t, J=7.27 Hz, 2H), 0.89 (t, J=7.27 Hz, 3H).

(2Z4E)-N-butyl-2-cinnamamido-5-phenylpenta-2,4-dienamide (CAB-42)

$^1$H NMR (850 MHz, DMSO-d$_6$) δ 9.67 (s, 1H), 8.00 (t, J=5.45 Hz, 1H), 7.64 (d, J=7.27 Hz, 2H), 7.51-7.54 (m, 3H), 7.44-7.48 (m, 2H), 7.39-7.42 (m, 1H), 7.35-7.39 (m, 2H), 7.27-7.31 (m, 1H), 7.02 (dd, J=11.16, 15.83 Hz, 1H), 6.89-6.92 (m, 1H), 6.72 (d, J=11.42 Hz, 1H), 3.20-3.25 (m, 1H), 3.11-3.15 (m, 2H), 0.94 (t, J=7.27 Hz, 2H), 0.89 (t, J=7.27 Hz, 3H).

(2Z4E)-2-cinnamamido-N-isopropyl-5-phenylpenta-2,4-dienamide (CAB-43)

$^1$H NMR (850 MHz, DMSO-d$_6$) δ 9.65 (br. s., 1H), 7.82 (d, J=7.78 Hz, 1H), 7.64 (d, J=7.27 Hz, 1H), 7.51-7.54 (m, 2H), 7.46 (t, J=7.53 Hz, 2H), 7.43 (d, J=7.27 Hz, 1H), 7.37 (t, J=7.79 Hz, 2H), 7.27-7.30 (m, 1H), 7.02 (dd, J=11.16, 15.83 Hz, 1H), 6.88 (s, 1H), 6.89 (s, 1H), 6.66 (d, J=11.42 Hz, 1H), 3.93-3.98 (m, 1H), 2.58-2.60 (m, 1H), 2.52-2.53 (m, 1H), 2.42-2.44 (m, 1H), 2.09 (s, 1H), 1.11 (d, J=6.23 Hz, 4H).

General Procedure for Synthesis of N-Aryl CAB Compounds Presented in Scheme 2 (CAB-32, CAB-36 and CAB-40)

Oxazolone 1 (2 mmol) and aniline derivative (2 mmol) were mixed with 5 mL DMF. The reaction was heated to 100° C. while stirring for 2 h and monitored by TLC. After cooling, the mixture was added slowly to ice-cold water. The resulting solid was collected by filtration, washed with water and purified using silica gel chromatography (petroleum ether/dichloromethane (DCM)/MeOH, gradient).

(2Z,4E)-2-cinnamamido-N-(4-methoxyphenyl)-5-phenylpenta-2,4-dienamide (CAB-32)

$^1$H NMR (400 MHz, DMSO-d$_6$) δ 9.87 (d, J=16.31 Hz, 1H), 7.66 (d, J=6.78 Hz, 2H), 7.59-7.63 (m, 2H), 7.52-7.59 (m, 2H), 7.43-7.51 (m, 2H), 7.40 (t, J=7.53 Hz, 2H), 7.29-7.35 (m, 1H), 7.11-7.20 (m, 1H), 6.89-7.00 (m, 3H), 6.76 (d, J=11.29 Hz, 1H), 3.75 (s, 2H).

(2Z,4E)-2-cinnamamido-N-(3-cyanophenyl)-5-phenylpenta-2,4-dienamide (CAB-36)

$^1$H NMR (850 MHz, DMSO-d$_6$) δ 10.02 (s, 1H), 8.18 (s, 1H), 7.99 (d, J=7.79 Hz, 1H), 7.65 (d, J=7.27 Hz, 1H), 7.51-7.60 (m, 4H), 7.47 (s, 2H), 7.37-7.45 (m, 5H), 7.31-7.37 (m, 2H), 7.20 (dd, J=11.42, 15.57 Hz, 1H), 7.00 (d, J=15.57 Hz, 1H), 6.91 (d, J=16.09 Hz, 1H).

(2Z,4E)-2-cinnamamido-N-(3-methoxyphenyl)-5-phenylpenta-2,4-dienamide (CAB-40)

$^1$H NMR (850 MHz, DMSO-d$_6$) δ 10.08 (s, 1H), 7.63 (d, J=7.27 Hz, 2H), 7.52-7.57 (m, 3H), 7.45-7.49 (m, 2H), 7.43 (d, J=7.27 Hz, 1H), 7.38 (t, J=7.79 Hz, 2H), 7.27-7.30 (m, 1H), 7.24 (dd, J=10.90, 15.57 Hz, 1H), 6.87 (d, J=16.09 Hz, 1H), 6.78 (d, J=15.05 Hz, 1H), 6.07 (d, J=11.42 Hz, 1H), 3.46 (t, J=6.49 Hz, 3H), 1.81-1.86 (m, 4H)

Synthesis of Ethyl (2Z,4E)-2-cinnamamido-5-phenylpenta-2,4-dienoate (CAB-21, Presented in Scheme 3)

The oxazolone 1 (2 mmol) was placed in round-bottom flask, added ethanol (10 mL) and 4-(N,N-dimethylamino)pyridine (DMAP). The mixture was heated at reflux for 2 h. The solvent was evaporated under vacuum and the product was purified by silica gel chromatography (petroleum ether/dichloromethane (DCM)/MeOH, gradient) to provide white solid.

$^1$H NMR (400 MHz, DMSO-d$_6$) δ 9.88 (s, 1H), 7.66 (dd, J=1.51, 7.78 Hz, 2H), 7.53-7.62 (m, 3H), 7.43-7.51 (m, 3H), 7.37-7.43 (m, 2H), 7.29-7.37 (m, 1H), 7.07-7.12 (m, 2H), 6.95-7.02 (m, 1H), 6.87 (d, J=15.81 Hz, 1H), 4.19 (q, J=7.11 Hz, 2H), 1.25 (t, J=7.15 Hz, 3H).

Biological Screening

Efflux pump inhibition (EPI) screening methodology:
Bacterial isolate. *Pseudomona aeruginosa* ATCC 27853 stored at −70° C. in Trypticase soy broth supplemented with 10% glycerol was recovered for testing.

Tests performed. Cup diffusion assay was performed to assess interaction between Ciprofloxacin CPX and 24 compounds. CPX minimum inhibitory concentrations (MICs) were determined alone and in the presence of each compound at concentrations ranging from 2000 to 62.5 μg/mL against *P. aeruginosa*. A fixed concentration of 200 μM of each compound was selected for testing.

Briefly, Petri dishes (90 mm) were filled with 25 mL Muller-Hinton agar containing 1 mL bacterial culture (1×10$^6$ CFU/mL) and 200 µM of each compound. The strains were inoculated separately. Six holes (5 mm in diameter) were made in the seeded agar plates. The holes were then filled with 20 of each concentration of CPX, plate with CPX only was served as control. Dishes were then incubated for 24 h at 37° C. The MIC was recorded as the lowest concentration that inhibits the growth of the bacterial strains. An efflux pump-inhibitory activity was defined as any compound exhibiting at least a twofold decrease in MIC to CPX when tested in the presence of the compound. All assays were performed in triplicate and MIC's values are given in µg/mL. The inhibition zone was measured using a caliper.

Pseudomonas aeruginosa Liquid Killing Assays on C. elegans

In vivo EPI activity of compounds that illustrated an MIC against *P. aeruginosa*. ATCC 27853 were tested on *C. elegans* using the liquid killing assay (LKA). Briefly, eggs of *C. elegans* were hatched on lawns of *E. coli* OP50 on nematode growth medium agar. Worms were grown to L4 stage by incubation at 25° C. for 48 h. Worms were washed off the plate with M9 buffer, deposited onto lawns of *E. coli* OP50 or *P. aeruginosa*. ATCC 27853 and the plates were incubated at 25° C. for 16 h. OP50-fed or *P. aeruginosa*-infected worms were washed from the plate with M9 buffer, allowed to settle to bottom of Eppendorf tubes, and rinsed with M9 buffer. The M9 was then removed and worms were resuspended in 5 mL liquid killing medium (80% M9 and 20% nematode growth medium (NGMII)) and 95 µL aliquots with approximately 50 worms were added to the wells of 96-microtiter plates with or without test compounds at the indicated concentration ranges (starting from 200 µM) in presence of sub-MIC concentration of CPX (100 µg/mL). As a control, worms treated without test compound contained an equivalent amount of DMSO in the assay medium. Plates were scored for live worms at the time of inoculation and incubated at 37° C. for 24 h. Using a dissecting microscope, worms were considered dead if they appeared straight, and alive if they appeared S-shaped and were moving.

Rhodamine123 (R123) Efflux Assay

The cells ($10^5$) were counted and suspended in 1 ml RPMI medium. The appropriate CAB derivative (0.5 µM) was added to the medium alongside 1, 5 or 10 µM WYE-354, or 100 µM Verapamil as control inhibitors and incubated for 60 min at 37° C. Upon dye uptake, the cells were pelleted by centrifugation at 250×g for 5 min at 4° C. in a cold centrifuge. The harvested cells were washed twice with 1X ice-cold PBS and resuspended in 1 ml RPMI with the inhibitors alone, and reincubated for an additional 60 min at 37° C. to allow the efflux of R123. The cells were subsequently washed twice with ice-cold PBS and analyzed immediately on a BD FACSAria III. A minimum of 5,000 events were recorded for analysis.

Results and Discussion

The agar plate diffusion test (Zou, He et al. 2019) was utilized to qualitatively evaluate the ciprofloxacin killing effect on MDR-Pa in absence (control) and in presence of our designed efflux pump inhibitors. Results showed that several compounds had significant increase in bacterial inhibition zone (FIG. 2A-K). CAB-30, the analogue that was previously reported as a potent Pgp inhibitor demonstrated the highest chemosensitization in this test.

The structure-activity relationship (SAR) confirmed that N-aliphatic derivatives CAB-30 (N-propyl) was the most potent compound to enhance CPX antibiotic activity followed by, CAB-37 (N-(β-hydroxyethyl)), CAB-38 (1-morpholinyl), CAB-41 (1-pyrrolidinyl), CAB-42 (N-butyl) which had similar activities. Meanwhile, the N-aryl derivatives CAB-32 and CAB-40 along with the ester CAB-21 showed weak activities. The exception was the N-(m-cyanophenyl) derivative CAB-36 which showed moderate chemosensitization activities. However, this compound had poor solubility compared to N-aliphatic congeners. We decided to focus on the N-aliphatic compounds because they give an opportunity to improve physicochemical properties, drug-likeness and solubility. For instance, the activities were acceptable for CAB-37 and CAB-38, two derivatives carrying molar substituents. Therefore, they were considered for further investigations. It is worthy to mention that our compounds never showed antibiotic activity if tested alone (in the absence of CPX).

Protection of *Caenorhabditis elegans* (*C. elegans*) Against the Killer MDR-Pa Infection.

*C. elegans* is a very efficient whole organism test. The worm develops several reliable disease pathways and can be recruited to measure therapeutic activities of compounds. The technique bears several advantages such as low cost, there is no need for special growth or assay conditions (c.f. animal house and expensive caring for in vivo test on mammalians such as rats) (Kaletta and Hengartner 2006) and there are no ethical issues with consuming animals. In our particular assay, *C. elegans* can be infected and killed by Pa, and therefore, can be used for identifying compounds that help to protect the worm from pathogenic bacteria (Ewbank and Zugasti 2011).

TABLE 1

Assay of chemosensitization of MDR-Pa in *C. elegans* whole organism model assay.

| CAB Code | C. elegans + 100 µg/mL CPX) MIC (µM) | Survival x/50 in presence of CAB compounds | | | | | | | |
|---|---|---|---|---|---|---|---|---|---|
| | | at 200 µM | at 100 µM | at 50 µM | at 25 µM | at 12.5 µM | at 6.25 µM | at 3.125 µM | at 1.562 µM |
| CAB-30 | 1.56 | 50 | 40 | 40 | 40 | 20 | 20 | 20 | 20 |
| CAB-35 | 200 | 15 | | | | | | | |
| CAB-36 | Died | | | | | | | | |
| CAB-37 | 50 | | | | | | | | |
| CAB-38 | 25 | | 40 | 10 | 5 | 3 | | | |
| CAB-40 | 200 | 25 | | | | | | | |
| CAB-41 | 50 | | 25 | 7 | 5 | | | | |
| CAB-42 | 100 | | 45 | 5 | | | | | |
| CAB-43 | Died | | | | | | | | |
| Control (Cipro Only) | Died | | | | | | | | |

We used the assay to measure the CAB N-alkyl derivatives CAB-30, CAB-35, CAB-36, CAB-37, CAB-38, CAB-40, CAB-41, CAB-42 and CAB-43 ability to protect *C. elegans* against MDR-Pa. Results (Table 1) showed that the non-selective Pgp and RND inhibitor CAB-30 was highly potent to increase survival and maintain motility of *C. elegans*. In terms of survival, CAB-30's MIC was 1.56 µM followed by CAB-38 (MIC=25 µM). Result showed that CAB-30 is the highest potency followed by CAB-38 (morpholino derivative). Unfortunately, CAB-37 (N-hydroxyethyl derivative) did not show any activity in *C. elegans* model. CAB-38, which contains a more polar morpholino group, showed higher activity than CAB compounds with N-hydrophobic substituents such as CAB-41 CAB-42 or CAB-43. CAB-38 was considered the best selection for further investigation because it had promising activities and improved solubility.

Selectivity Test on Pgp Expressing Human Cancer Cells.

Figure 3A:
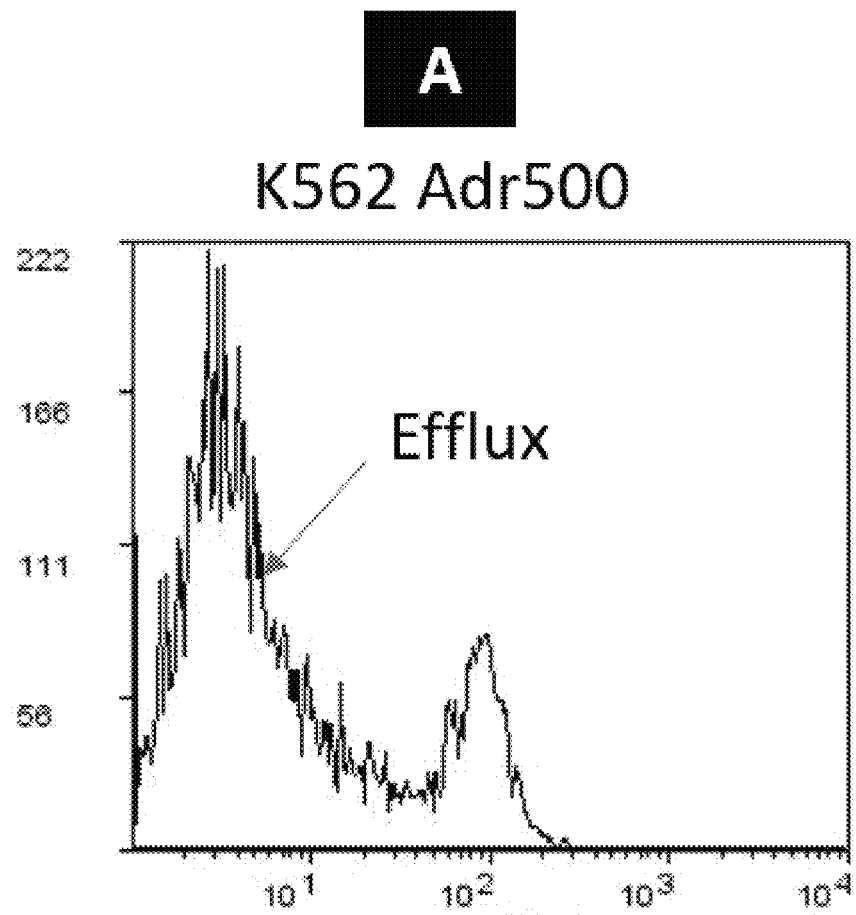
FIG. 3A-C. Effect of CAB-38 on human efflux Pgp protein. (A) Negative Control retention of R123 dye within highly resistant K562 Adr500 cells. (B) Positive Control showing large increase of R123 dye after addition of everolimus, a Pgp inhibitor. (C) Test experiment by addition of CAB-38 showing similar diagram to the negative control (not retention of R123 dye).
Figure 3B:
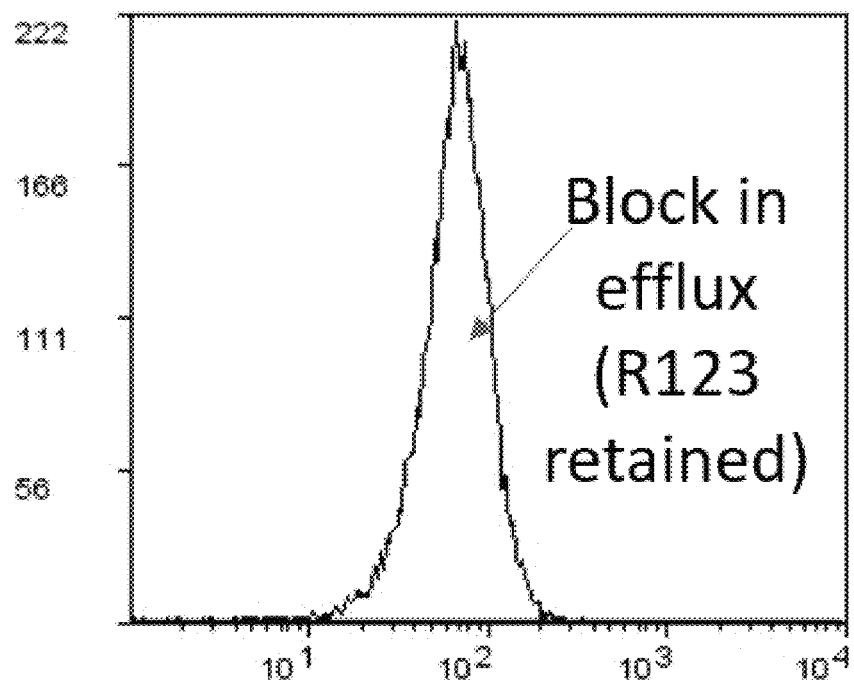
Figure 3C:
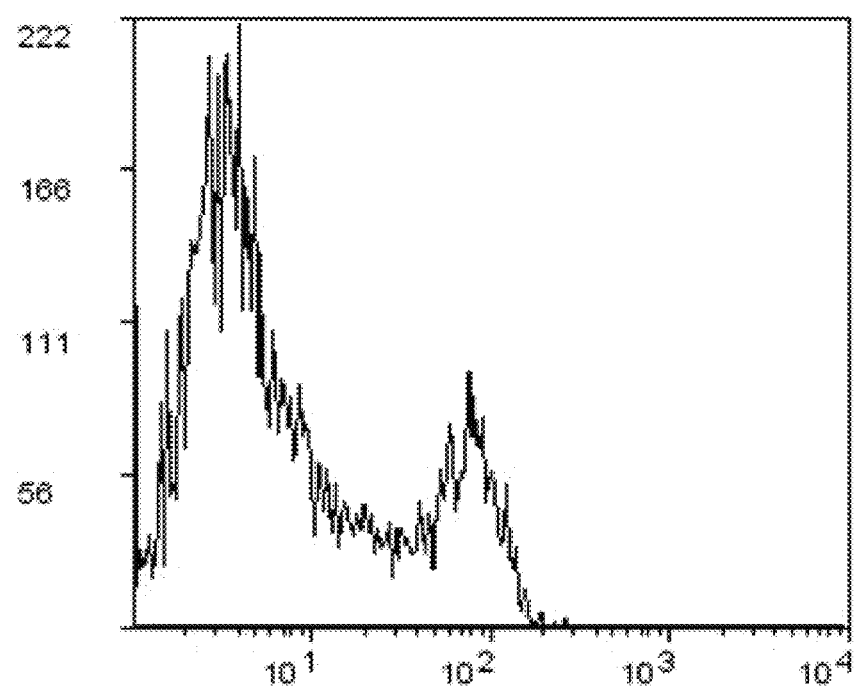

CAB-30 had undesired Pgp inhibition activities (El-Araby, Omar et al. 2017) and could not be further studied. We studied the selectivity of CAB-38 by testing its Pgp inhibition (human efflux protein) activities. This assay was performed by measuring the retention of Rhodamine123 (R123) dye (substrate of Pgp) in human leukemia cell lines K562. The negative control of experiment is composed of highly resistant cells K562 Adr500 which keep R123 outside the cancer cells (FIG. 3A). The positive control is performed by repeating the same experiment after incubation of cells with everolimus sub-cytotoxic dose, a powerful Pgp inhibitor (FIG. 3B). The test compound was incubated with K562 Adr500 and then added R123 dye. The cell content of R123 showed clearly that CAB-38 was a poor inhibitor of Pgp because it did not cause entrapment of the dye inside cells (FIG. 3C). Therefore, CAB-38 can be concluded to have selective inhibition against bacterial efflux pump over human efflux pump.

CONCLUSION

In this invention, we identified a new approach to suppress multidrug resistance of Pa. CAB-38 was slightly less potent that CAB-30 but it had two great advantages: it is more polar and it is selective against bacteria with no inhibition observed in human cancer cells producing Pgp.

REFERENCES (WHO). "2019: A Year of Challenges and Change." *MEDICC Rev* 21(1): 3.
Adedeji, W. A. (2016). "The Treasure Called Antibiotics." *Annals of Ibadan postgraduate medicine* 14(2): 56-57.
Bhardwaj, A. K. and P. Mohanty (2012). "Bacterial efflux pumps involved in multidrug resistance and their inhibitors: rejuvinating the antimicrobial chemotherapy." *Recent Pat. Anti-Infect. Drug Discovery* 7(1): 73-89.
Daury, L., F. Orange, J.-C. Taveau, A. Verchere, L. Monlezun, C. Gounou, R. K. R. Marreddy, M. Picard, I. Broutin, K. M. Pos and O. Lambert (2016). "Tripartite assembly of RND multidrug efflux pumps." *Nat. Commun.* 7: 10731.
El-Araby, M. E., A. M. Omar, M. T. Khayat, H. A. Assiri and A. M. Al-Abd (2017). "Molecular Mimics of Classic P-Glycoprotein Inhibitors as Multidrug Resistance Suppressors and Their Synergistic Effect on Paclitaxel." *PLoS One* 12(1): e0168938.
Ewbank, J. and O. Zugasti (2011). *C. elegans*: model host and tool for antimicrobial drug discovery. Dis Model Mech 4: 300-304.
Kaletta, T. and M. O. Hengartner (2006). "Finding function in novel targets: *C. elegans* as a model organism." *Nature reviews Drug discovery* 5(5): 387-399.
Matos, E. C. O., R. B. Andriolo, Y. C. Rodrigues, P. D. L. Lima, I. Carneiro and K. V. B. Lima (2018). "Mortality in patients with multidrug-resistant *Pseudomonas aeruginosa* infections: a meta-analysis." *Rev Soc Bras Med Trop* 51(4): 415-420.
Pang, Z., R. Raudonis, B. R. Glick, T.-J. Lin and Z. Cheng (2019). "Antibiotic resistance in *Pseudomonas aeruginosa*: mechanisms and alternative therapeutic strategies." *Biotechnology Advances* 37(1): 177-192.
Ramirez, C. A., J. L. Bran, C. R. Mejia and J. F. Garcia (1985). "Open, prospective study of the clinical efficacy of ciprofloxacin." *Antimicrob Agents Chemother* 28(1): 128-132.
Tacconelli, E., E. Carrara, A. Savoldi, S. Harbarth, M. Mendelson, D. L. Monnet, C. Pulcini, G. Kahlmeter, J. Kluytmans, Y. Carmeli, M. Ouellette, K. Outterson, J. Patel, M. Cavaleri, E. M. Cox, C. R. Houchens, M. L. Grayson, P. Hansen, N. Singh, U. Theuretzbacher and N. Magrini (2018). "Discovery, research, and development of new antibiotics: the WHO priority list of antibiotic-resistant bacteria and tuberculosis." *Lancet Infect Dis* 18(3): 318-327.
Venter, H. (2019). "Reversing resistance to counter antimicrobial resistance in the World Health Organisation's critical priority of most dangerous pathogens." *Biosci Rep* 39(4).
Wang, Y., H. Venter and S. Ma (2016). "Efflux Pump Inhibitors: A Novel Approach to Combat Efflux-Mediated Drug Resistance in Bacteria." *Curr. Drug Targets* 17(6): 702-719.
Wieland, K., P. Chhatwal and R.-P. Vonberg (2018). "Nosocomial outbreaks caused by *Acinetobacter baumannii* and *Pseudomonas aeruginosa*: Results of a systematic review." *American Journal of Infection Control* 46(6): 643-648.
Zou, H., J.-t. He, B.-n. He, T.-y. Lao, F. Liu and X.-y. Guan (2019). "Sensitivity assessment of denitrifying bacteria against typical antibiotics in groundwater." *Environmental Science: Processes & Impacts* 21(9): 1570-1579.

While the invention has been described in terms of its several exemplary embodiments, those skilled in the art will recognize that the invention can be practiced with modification within the spirit and scope of the appended claims. Accordingly, the present invention should not be limited to the embodiments as described above but should further include all modifications and equivalents thereof within the spirit and scope of the description provided herein.

FUNDING STATEMENT

This Project was funded by the Deanship of Scientific Research (DSR), at King Abdulaziz University, Jeddah, Saudi Arabia, under grant no. G-523-166-1439. The authors, therefore, acknowledge with thanks DSR for technical and financial support.

We claim:

1. A method of preventing or treating an infection caused by *Pseudomonas aeruginosa* (Pa) in a subject in need thereof, comprising
administering to the subject a compound of Formula I and an antibiotic, wherein the compound of Formula I has the following structure:

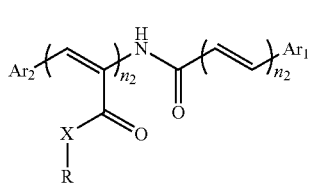

FORMULA I and salts, hydrates and stereoisomers thereof,
wherein
Ar1 and Ar2 may be the same or different and are a substituted or unsubstituted aryl or heteroaryl;
X is
i) N, O, S or C and R is substituted or unsubstituted, saturated or unsaturated, branched or unbranched C1-C10 alkyl; a 5-8 carbon unicyclic ring that is substituted or unsubstituted, saturated or unsaturated, cyclic alkyl or heterocyclic; or a 10-12 carbon polycyclic ring that is substituted or unsubstituted, saturated or unsaturated, cyclic alkyl or heterocyclic;

or ii) X and R are atoms of a 5-8 carbon unicyclic ring that is substituted or unsubstituted, saturated or unsaturated, cyclic alkyl or heterocyclic; or a 10-12 carbon polycyclic ring that is substituted or unsubstituted, saturated or unsaturated, and cyclic alkyl or heterocyclic;

and n1 and n2 are the same or different and =1 or 2.

2. The method of claim 1, wherein the Pa is a multidrug resistant (MDR) Pa.

3. The method of claim 1, wherein Ar1 and Ar2 are phenyl; n1=1; n2=2; and X=N or O.

4. The method of claim 1, wherein X=N and R=substituted or unsubstituted, saturated or unsaturated, branched or unbranched C1-C10 alkyl; substituted phenyl; or N and R are atoms in a ring structure.

5. The method of claim 1, wherein X=O and R=substituted or unsubstituted, saturated or unsaturated, branched or unbranched C1-C10 alkyl.

6. The method of claim 1, wherein the compound is

CAB-30

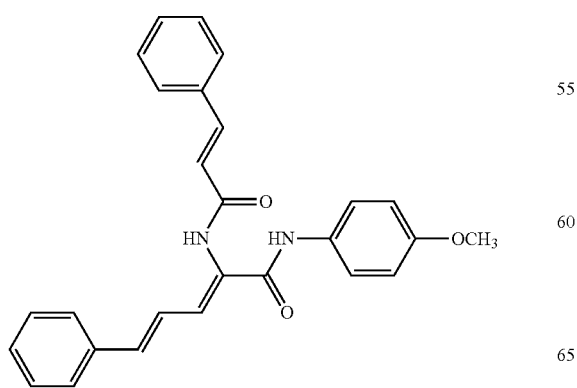

CAB-32

CAB-35

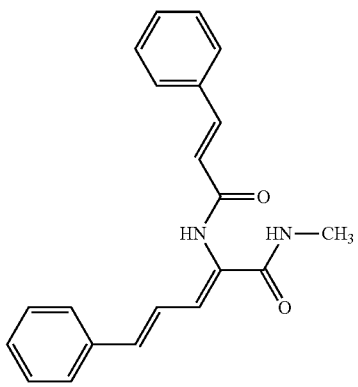

CAB-36

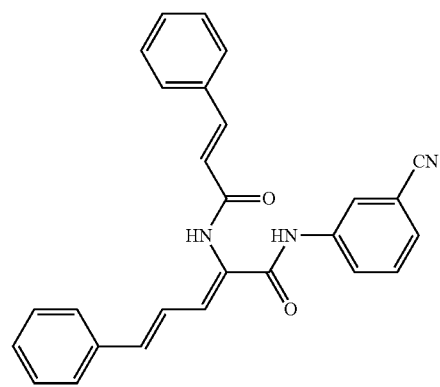

CAB-37

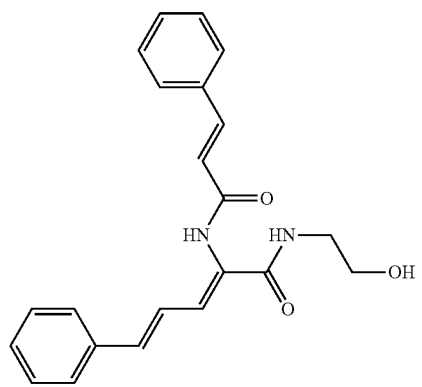

CAB-38

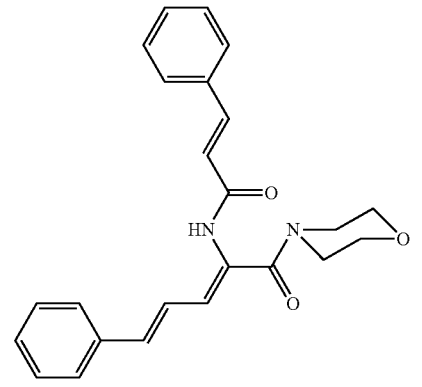

-continued

CAB-40
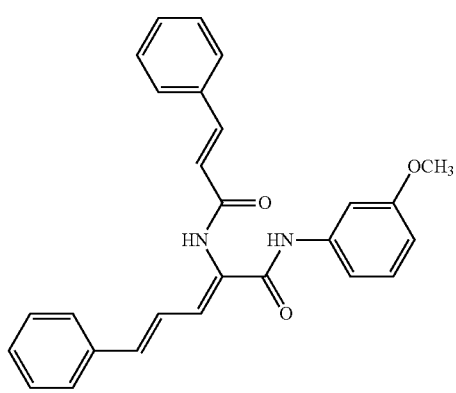

CAB-41
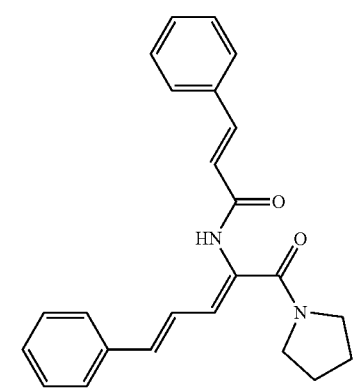

CAB-42
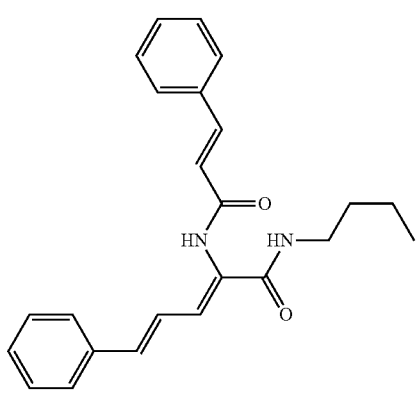

CAB-43
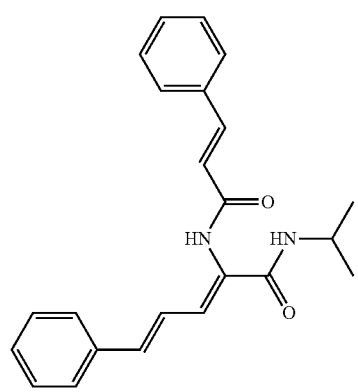
or

-continued

CAB-21
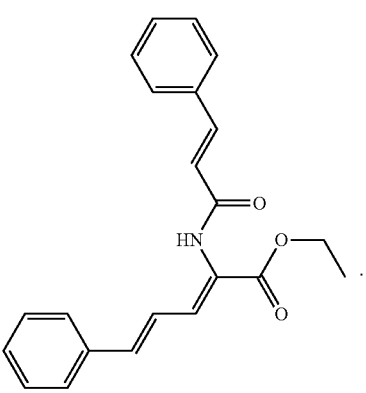

7. A method of inhibiting the efflux of an antibiotic from a bacterium, comprising
contacting the bacterium containing the antibiotic with a compound of Formula I:

FORMULA I
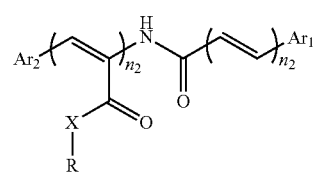

and salts, hydrates and stereoisomers thereof,
wherein
Ar1 and Ar2 may be the same or different and are a substituted or unsubstituted aryl or heteroaryl;
X is
i) N, O, S or C and R is substituted or unsubstituted, saturated or unsaturated, branched or unbranched C1-C10 alkyl; a 5-8 carbon unicyclic ring that is substituted or unsubstituted, saturated or unsaturated, cyclic alkyl or heterocyclic; or a 10-12 carbon polycyclic ring that is substituted or unsubstituted, saturated or unsaturated, cyclic alkyl or heterocyclic; or
ii) X and R are atoms of
a 5-8 carbon unicyclic ring that is substituted or unsubstituted, saturated or unsaturated, cyclic alkyl or heterocyclic; or
a 10-12 carbon polycyclic ring that is substituted or unsubstituted,
saturated or unsaturated, and cyclic alkyl or heterocyclic;
and
n1 and n2 are the same or different and =1 or 2.

8. The method of claim 7, wherein the bacterium is a multidrug resistant (MDR) Pa.
9. The method of claim 7, wherein the antibiotic is ciprofloxacin.
10. The method of claim 1 wherein the antibiotic is ciprofloxacin.

* * * * *